United States Patent [19]
Whiteside et al.

[11] Patent Number: 5,772,663
[45] Date of Patent: Jun. 30, 1998

[54] SURGICAL DEVICE FOR BANDING BONE WITH CABLE

[76] Inventors: Leo A. Whiteside, 14825 Sugarwood Trail, Chesterfield, Mo. 63017; Stephen E. White, 1147 Richland Meadows Dr., Ballwin, Mo. 63021

[21] Appl. No.: 818,277

[22] Filed: Mar. 17, 1997

Related U.S. Application Data

[63] Continuation of Ser. No. 197,738, Feb. 17, 1994, abandoned.

[51] Int. Cl.[6] ............................................. A61B 17/56
[52] U.S. Cl. ............................................. 606/74; 606/103
[58] Field of Search ............................................. 606/74, 72, 61, 606/60, 86, 103, 102, 140, 144, 142, 148, 151, 157, 158, 228, 232

[56] References Cited

U.S. PATENT DOCUMENTS

| | | |
|---|---|---|
| 3,111,945 | 11/1963 | von Solbrig . |
| 3,507,270 | 4/1970 | Ferrier ................................. 606/74 X |
| 3,570,497 | 3/1971 | Lemole ................................. 606/74 X |
| 3,709,218 | 1/1973 | Halloran . |
| 3,997,138 | 12/1976 | Crock et al. . |
| 4,047,523 | 9/1977 | Hall . |
| 4,047,524 | 9/1977 | Hall . |
| 4,057,863 | 11/1977 | Bewley ................................. 7/132 |
| 4,119,091 | 10/1978 | Partridge ................................. 606/74 X |
| 4,128,100 | 12/1978 | Wendorff . |
| 4,146,022 | 3/1979 | Johnson et al. . |
| 4,269,180 | 5/1981 | Dall et al. . |
| 4,535,764 | 8/1985 | Ebert . |
| 4,587,963 | 5/1986 | Leibinger et al. . |
| 4,606,335 | 8/1986 | Wedeen ................................. 606/74 X |
| 4,667,662 | 5/1987 | Titone et al. . |
| 4,790,303 | 12/1988 | Steffee . |
| 4,813,416 | 3/1989 | Pollak et al. . |
| 4,966,600 | 10/1990 | Songer et al. . |
| 5,116,340 | 5/1992 | Songer et al. . |
| 5,245,721 | 9/1993 | Lowe et al. ................................. 7/129 |
| 5,312,410 | 5/1994 | Miller et al. ................................. 606/86 |
| 5,395,374 | 3/1995 | Miller et al. ................................. 606/74 |

FOREIGN PATENT DOCUMENTS

| | | |
|---|---|---|
| 126455 | 1/1948 | Australia . |
| 548197 | 10/1957 | Canada . |
| 543126 | 8/1922 | France . |
| 26 44 735 | 4/1977 | Germany . |
| 3146634 | 6/1983 | Germany . |
| 3244680 | 6/1984 | Germany ................................. 606/74 |
| 4024334 | 2/1992 | Germany ................................. 606/74 |
| 7610576 | 3/1978 | Netherlands . |
| 425604 | 6/1967 | Switzerland . |
| 2207055 | 1/1989 | United Kingdom . |

OTHER PUBLICATIONS

Danek brochure "Songer Titanium Cable System" date and author unknown, 2 pages.
Howmedica brochure "The Dall–Miles Trochenter Cable Grip System" date and author unknown, pp. 1–10.
Codman & Shurtleff, Inc. brochure "Sof'wire Cable System" Jun. 1992, author unknown, 6 pages.
Acumed, Inc. brochure "Osteo–Clage Cerclage Cable System" Jul. 1992, author unknown, 4 pages.

*Primary Examiner*—Guy V. Tucker

[57] ABSTRACT

A bone cable strap and surgical instruments pass the cable strap around a bone, tension it, fasten it and trim the excess cable. The surgical instruments include: a cable passer which has an arcuate guiding member having a groove facing the bone to guide the cable around the bone; a cable tensioner having concentric tubular members with a cable clamp at one end, a nipple at the other end, and a handle in between such that turning the handle spreads the cable clamp away from the nipple; and a combination cable crimper-cutter having jaws with both crimping and cutting edges. The cable strap is comprised of a flexible cable having a ferrule pre-affixed to one end. The cable is passed under the bone using the cable passer. The free end of the cable is passed through the ferrule and the cable tensioner is used to draw the cable tight around the bone. The crimper-cutter is then used to fasten the ferrule in place about the cable and trim the excess cable.

20 Claims, 2 Drawing Sheets

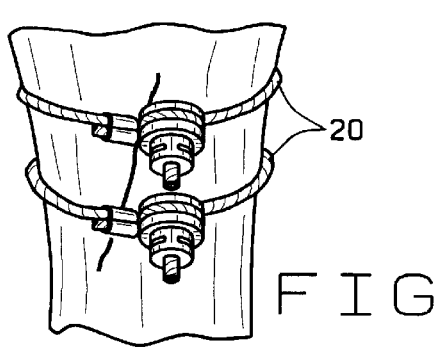
FIG. 1
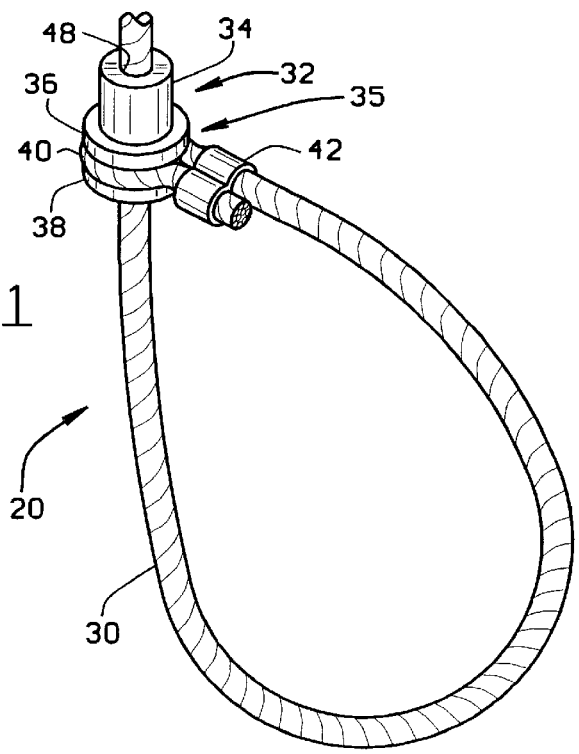
FIG. 2
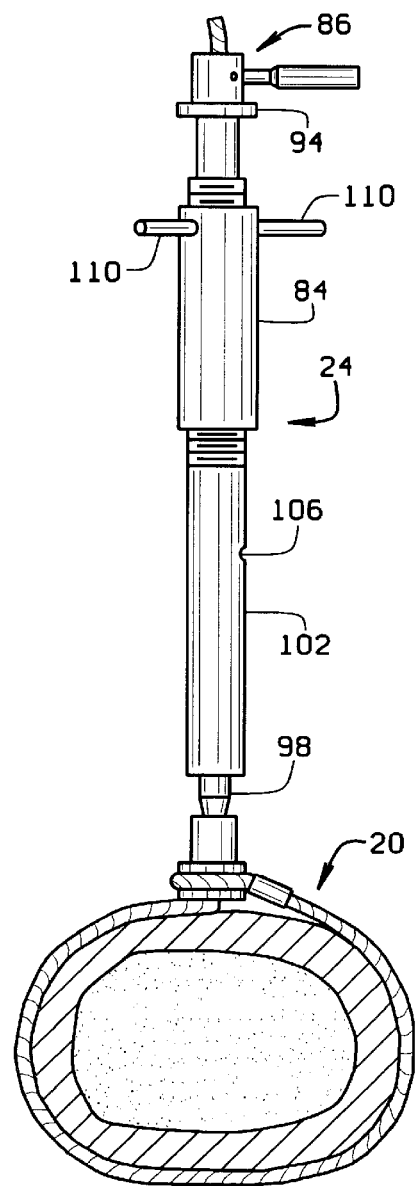
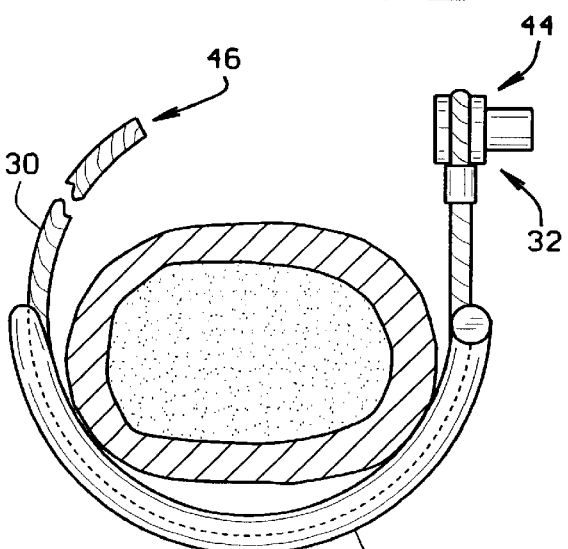
FIG. 3
FIG. 4

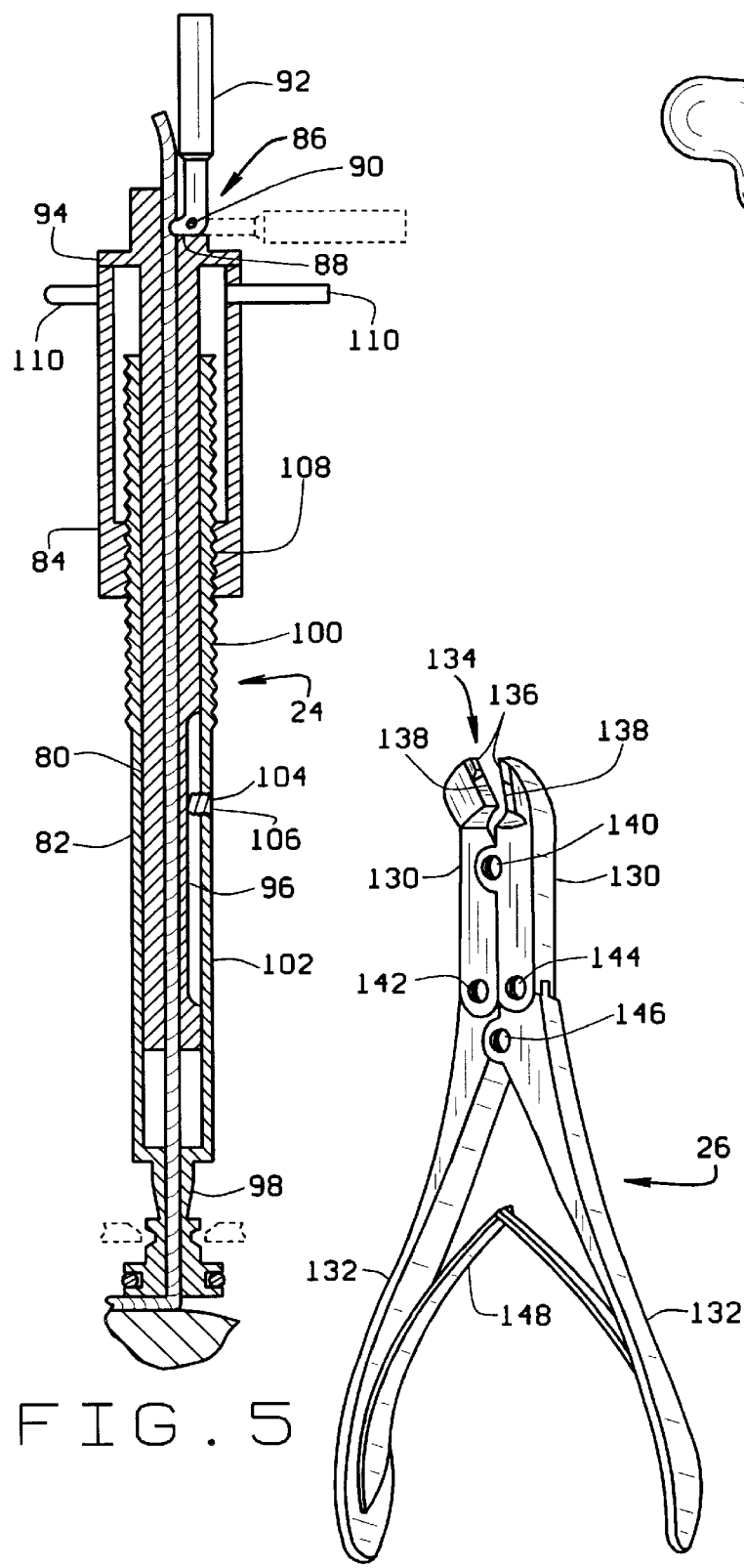
FIG. 5
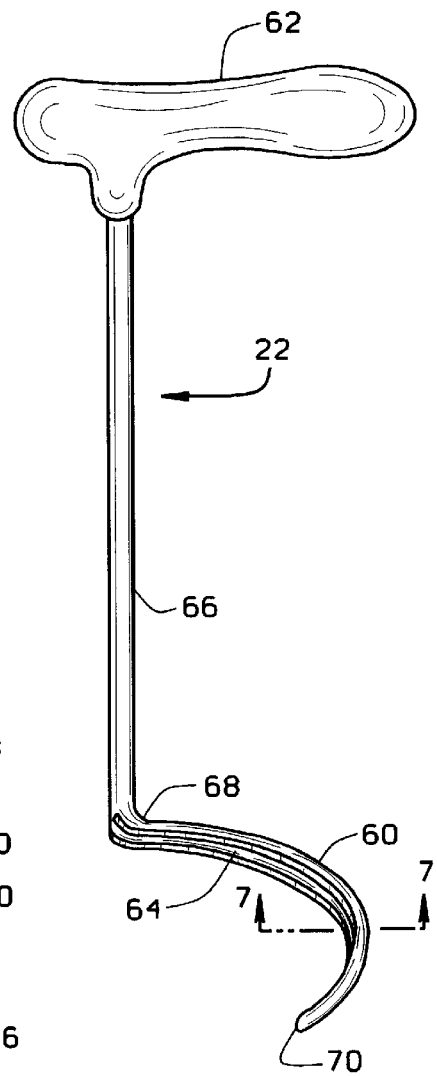
FIG. 6
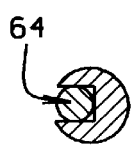
FIG. 7
FIG. 8

SURGICAL DEVICE FOR BANDING BONE WITH CABLE

This application is a continuation of application Ser. No. 08/197,738 filed on Feb. 17, 1994 now abandoned.

BACKGROUND AND SUMMARY OF THE INVENTION

In the hands of a skilled surgeon, surgical instruments may be used to repair or replace broken or damaged joints and limbs. Typically, these instruments are specifically designed for particular surgical tasks to improve the quality of the result, as well as to make the surgeon's job easier and faster. These latter two attributes produce hidden advantages. Making the surgeon's job easier reduces the surgeon's fatigue thereby conserving the surgeon's strength and alertness to ensure optimum performance throughout the entirety of lengthy surgeries. Saving time is of importance in surgical endeavors because risk to the patient is reduced by shortening the surgery. In addition, surgical instruments must be reliable and preferably they should be inexpensive.

One of the tasks encountered by surgeons is temporarily fastening pieces of bone together with cable. Primarily, this task arises in two settings, one being a bone fracture wherein the fragments may be temporarily joined by looping a cable around the fragments, drawing the loop tight about the fragments and fastening the cable to hold the fragments in place. The other setting occurs during implant surgery wherein the bones need reinforcement to prevent them from splintering during the insertion of the implants and to hold the implant in place after insertion. This is accomplished in much the same way as when fastening the fragments; the cable is looped around the bone, drawn tight, and fastened.

Several systems have been developed for performing the task described above. One such system uses a cable sleeve to fasten the cable in place. The configuration of this cable sleeve is that of a malleable metal block with two holes having parallel centerlines extending lengthwise through the block. The holes have diameters slightly larger than the cables so that the cable may be threaded through the holes. As the sleeve is malleable, the sleeve may be crimped against the cable to fasten the cable in position.

Several surgical instruments specifically designed for use with this cable system are available as a set. One instrument in this set is a cable passer which is generally comprised of an arcuate tube with a straight handle similar to a common screwdriver. A second instrument in the set is a cable tensioner which is a forked instrument having pulleys at the ends of each branch of the fork. At the end of the tensioner opposite the fork is a crank and between the pulleys and the crank are two clamps. Turning the crank in one direction moves the clamps towards the pulleys, and turning the crank in the other direction moves the clamps away from the pulleys. A third surgical instrument in the set is a crimping tool which is a fairly typical pair of pliers having jaws with blunt teeth for crimping the cable sleeve once it is in place about the bone. A fourth instrument is a rotary cable cutter. This cutter is comprised of two concentric cylinders with aligned holes extending radially through them and opposing plier-type grips. When the grips are brought together, an internal mechanism rotates the cylinders thereby shearing anything protruding through the holes.

This prior art system has several disadvantages. Since the cable sleeve is a separate piece, unattached to the cable, and small, it is susceptible to being dropped and lost. If this happens, the surgical team must spend time looking for the fastener because everything must be accounted for during surgery to prevent instruments and materials from being left inside the patient. In addition, the size of the sleeve makes handling it difficult. Therefore, the surgeon must concentrate and use care to prevent fumbling the sleeve thereby adding to the surgeon's fatigue. Further, the screwdriver-type handle of the cable passer is not ergonomically optimal because as the passer is inserted and withdrawn the surgeon's arm must pass through uncomfortable positions and make an unnatural movement. As this cable system has two loose ends, the tensioner must be a complicated apparatus so the cable ends can be pulled in opposite directions to draw the cable tightly around the bone.

A second prior art system uses cables which have a loop formed in one end by bending the cable back on itself and installing a cable sleeve over the cable to maintain the loop. This particular cable sleeve is a short tube having an internal diameter large enough to accept two cable diameters. When the sleeve is in the desired location, the sleeve is crimped to fasten it to the cable. As in the other prior art system, the fastener is loose and must be attached to the cable end by the surgeon. The ferrule has an annular flange at one end and an inner diameter slightly larger than the cable diameter so that the free cable end may be threaded therethrough and the ferrule crimped to fasten the cable in position. The diameter of the ferrule flange is greater than the inner diameter of the cable loop so that the ferrule cannot pass through the loop.

As with the first prior art cable system described above, several surgical instruments are available to use with this system. One surgical instrument used with the system is a cable tensioner. This tensioner is comprised of two concentric hollow members. The outer member has a nipple at one end configured to engage a ferrule. A cable clamp is provided on the inner member at the other end of the instrument from the nipple. A ratchet mechanism incrementally moves the cable clamp away from the nipple as the surgeon actuates the ratchet to tension the cable before crimping. Other instruments used with this system include a cable crimper similar to the one described above and a typical pliers-type cable cutter having opposing knife edge cutter teeth actuated by opposing grips.

As with the first cable system, the second cable system and associated surgical instruments have disadvantages. This cable system also uses separate fasteners which may be lost, thereby causing lost time and potential complications and liability as described above. In addition, the cable tensioner provided with this second system does not permit infinitely variable tension. Therefore, the surgeon must settle for a less than optimal cable tension, either being tighter or looser than desired. In addition, the ratchet mechanism of this cable tensioner is somewhat complicated, thereby being inherently susceptible to failure. Further, the system uses separate cable crimpers and cutters.

A third prior art cable system uses a cable with a looped end and a ferrule identical to the second system described above. This system is identical in all respects to the second system except that a combination tensioner-crimper is employed. The tensioner-crimper is similar to the cable crimper described above except that one handle of the crimper has a rotatable capstan which is driven by a worm gear and key. The rotatable capstan, worm gear and key are similar to the keys used on guitars to tighten the strings. Once the cable is threaded through the ferrule, the surgeon loosely grips the ferrule with the jaws of the tensioner-crimper and threads the cable through the capstan. Then the worm gear is rotated by turning the key to thereby rotate the capstan and draw the cable tight around the bone. When the desired tension is achieved, the pliers may be further actuated to crimp the ferrule in place about the cable. Once crimped the instrument may be removed and the free end of the cable may be trimmed as previously described. As with the other prior art systems, this system also uses a cable and a separate fastener, and the tensioner is complicated.

In order to solve these and other problems in the prior art, the inventor has succeeded in designing and developing a new cable system and surgical instruments to pass the cable under the bone, and tighten and affix the cable around the bone. The cable strap used with the system of the present invention is comprised of a flexible cable having a fastener attached to one end. Thus, unlike prior art cables, the fastener is not loose and therefore cannot become misplaced during surgery. In the preferred embodiment, the fastener is a ferrule.

A cable passer is provided for use with the cable system of the present invention. The passer has an arcuate section with a groove facing the center of the arc such that when the cable passer is inserted around the bone, the surgeon may insert the cable into either end of the groove first. Once the cable is in place, the passer may be withdrawn simply by removing the cable from the groove and retracting the passer. Thus, the passer of the present invention does not need to pass over an end of the cable to be withdrawn.

The surgical instruments of the present invention also include an elegantly simple cable tensioner having concentric hollow members. The inner member has a cable clamp and collar at one end and the outer member has external screw threads adjacent the cable clamp and a nipple opposite the cable clamp. A handle with internal threads is threaded onto the outer member threads such that as the handle is turned in one direction, it contacts the collar of the inner member and forces the cable clamp away from the nipple. Thus, to use the tensioner the surgeon simply threads the free end of the cable through the center of the inner member nipple and clamps it in place. Then by turning the handle, the clamp and nipple spread apart and tension the cable around the bone.

Another instrument provided for use with the cable system of the present invention is a combination cable crimper-cutter. This instrument is a pair of pliers having jaws with crimper teeth at one end and cutter teeth at the other end. This same instrument may be used, both to crimp the ferrule and cut the cable, thereby eliminating one of the tools. When the desired tension is achieved, the cable crimper-cutter is used to crimp the ferrule to fasten the cable in place. After the cable tensioner is removed, the cutter portion of the crimper-cutters is used to trim the free end of the cable.

While the principal advantages and features of the present invention have been briefly described above, a greater understanding of the novel and unique features of the invention may be obtained by referring to the drawings and Detailed Description of the Preferred Embodiment which follow.

BRIEF DESCRIPTION OF THE DRAWINGS

FIG. 1 is an orientation view the cable system of the present invention installed about a fractured bone;

FIG. 2 is an orthographic projection of the cable system of the present invention;

FIG. 3 is a cross-sectional view of the cable passer inserted around a bone with a cable strap inserted therein;

FIG. 4 is a front elevation view of the cable tensioner showing a cable strap surrounding a bone and inserted in the cable tensioner;

FIG. 5 is a cross-sectional view of the cable tensioner with cable strap therein and showing the open position of the cam lever and the combination crimper-cutter crimper teeth in phantom;

FIG. 6 is a front elevation view of the cable passer;

FIG. 7 is a cross-sectional view of the cable passer taken in the plane of line 7—7 of FIG. 6 showing the shape of the arcuate member and groove; and FIG. 8 is a perspective view of the combination cable crimper-cutters.

DETAILED DESCRIPTION OF THE PREFERRED EMBODIMENT

The cable system and surgical instruments of the present invention are generally comprised of cable straps 20 (FIG. 1), a cable passer 22 (FIG. 6), a cable tensioner 24 (FIG. 5), and a combination cable crimper-cutter 26 (FIG. 8). As shown in FIG. 2, the cable straps 20 are generally comprised of a flexible cable 30 with a ferrule 32 attached to one end. In the preferred embodiment, the ferrule 32 has a short malleable neck portion 34 opposite a head portion 35 having two annular flanges 36, 38. The flanges are spaced by a channel 40 which is approximately as wide as the cable is thick. One end of the cable 30 is looped around the ferrule and positioned within the channel 40. The end is doubled back upon itself as shown in FIG. 2 and a cable sleeve 42 is crimped around the cable adjacent the ferrule to permanently affix the ferrule to the cable end. The cable sleeve 42 is simply a tubular sleeve which has a circular or oblate cross-section. Once the sleeve is in place, a standard crimper tool, well known in the art, may be used to crimp the sleeve about the cable as shown in FIG. 2 to thereby maintain the correct size loop of cable. Thus installed, the flanges 36, 38 prevent the ferrule from separating from the cable. Hereinafter, the end of the cable with the fastener shall be referred to as the fastener end 44 and the end opposite the fastener shall be referred to as the free end 46. The ferrule 32 has a hole 48 extending through it of sufficient diameter that the cable can freely slide therethrough. As shall be described in greater detail later, the free end 46 may be threaded through the ferrule hole 48 and the short malleable neck portion 34 may be crimped about the cable to fasten the ferrule 32 in place. In the preferred embodiment, the cable is a surgical grade cobalt chromium alloy, however other materials such as stainless steel, titanium or other malleable metals may be used. The cable is approximately 12 to 20 inches in length and about 0.06 inches in diameter. Although the cable may be of the monofilament type or braided, in the preferred embodiment the cable is of the twisted type having seven strands of seven wires each. Alternate embodiments include other fastener types and ferrule configurations, as well as other means of attaching the fasteners to the cable.

As shown in FIG. 6, the cable passer 22 is generally comprised of an arcuate member 60 and a handle 62. The arcuate member has a groove 64 running the entire length of the arc and facing the center thereof. The passer also includes a stem portion 66 positioned between the arcuate member and handle. A bend 68 positions the handle out of the plane of the arc of the arcuate member so that the surgeon can insert the passer around the bone by a natural twisting motion of his forearm. In the preferred embodiment, the handle is a T-grip. Thus, the handle is positioned substantially parallel to and non-coplanar with the arcuate member. However, other handle configurations such as the straight grip as typically found on a screwdriver may also be used. In the preferred embodiment, the arcuate member has a bullet-nosed point 70 at the open end to ease insertion around the bone and its arc is approximately $2^{1/2}$ inches in diameter. This instrument, like the others in the set, is preferably made of surgical grade stainless steel. Variations may be made without departing from the scope of this invention.

Another instrument used in manipulating the cable is the cable tensioner 24 shown in FIG. 5. The tensioner is generally comprised of concentric inner and outer tubular members 80, 82 and a handle 84. The inner and outer tubular members 80, 82 are dimensioned to permit the inner member to freely slide within the outer member. At one end of the inner member 80 is a cable clamp 86 comprised of a cam 88 having an offset pivot 90 and a lever 92 to aid the surgeon in actuating the cam. Adjacent the cable clamp is an annular collar 94. A linear groove 96 is milled into the inner member for about half of its length opposite the cable clamp. A nipple 98 which is configured to engage the ferrule is formed in the outer tubular member opposite the cable clamp. The nipple 98 has a smaller diameter than the remainder of the outer member so that the ferrule, cable, and working area are not obstructed during tensioner use. Opposite the nipple, the outer member has external screw threads 100 extending for approximately half of its length. Between the threads and nipple is a knurled grip 102 of sufficient length to accommodate the width of a surgeon's palm. Approximately at the center of the outer member length is an opening 104 into which a pin 106 is pressfit. The pin is flush with the outer surface of the outer member but protrudes into the groove 96 of the inner member so that the inner and outer members cannot rotate relative to one another. The pin may take the form of a set screw threaded into the opening 104 or any other equivalent means for preventing relative rotation between the inner and outer members but permitting longitudinal relative motion. As seen in FIG. 5, the handle 84 is hollow and has internal threads 108 which engage the external threads of the outer member. The handle further has three equally spaced pins 110 extending radially outward from the handle to increase the amount of torque the surgeon may apply to the handle. As the handle is turned, it moves longitudinally along the outer member. When turned in one direction, the handle moves toward the cable clamp until it engages the annular collar 94. Thereafter, additional turns to the handle cause the inner member to move relative to the outer member. Thus, as the handle is turned the cable clamp and nipple spread apart. As with the other instruments, in the preferred embodiment the cable tensioner is made of surgical grade stainless steel. Alternate embodiments are easily envisioned which are within the scope of this invention. For example, the offset cam cable clamp may be replaced by a thumb screw which may be tightened against a cable extending through to the hollow of the inner member to thereby lock the cable in place.

Another surgical instrument included in this set is the combination crimper-cutter 26. As shown in FIG. 8, this instrument is generally comprised of jaws 130 and grips 132. The jaws have mating surfaces 134 having both crimper teeth 136 and cutter teeth 138. The cutter teeth are opposing knife edges positioned over the half of the mating surfaces nearest the grips. The other half of the mating surfaces comprise the crimper teeth which have substantially flat and parallel surfaces that do not contact when the jaws are closed. Instead, the crimper teeth are separated by approximately 0.04 inches. The jaws are hinged together at a first pivot 140. Opposite the mating surfaces are two more pivots 142, 144 which hinge the jaws to the grips. Near this second and third pivot is yet another pivot 146 which hinges the grips together. Thus configured, the pivots 140–146 provide a double lever action to give the surgeon significant mechanical advantage to reliably and securely crimp the ferrule and cut the cable. A leaf spring system 148 is welded between the grips to bias the grips and jaws apart. As with the other surgical instruments, the combination crimper-cutter is manufactured from surgical grade stainless steel in the preferred embodiment.

In order to use the cable system and surgical instruments, the surgeon prepares the area by exposing the patient's bone and performing any prerequisite tasks. The surgeon then grips the handle of the cable passer and inserts the arcuate member beneath the bone by hooking it around the bone and twisting his forearm until the point is exposed at the other side of the bone as shown in FIG. 3. Thus installed, the groove in the arcuate member is visible from one or both sides of the bone. The surgeon then takes a cable strap and inserts the free end into either end of the cable passer groove. As the cable is fed into the groove, the passer guides the cable around the bone until the free end is exposed out the other end of the groove. The resilience of the cable along with the bone and surrounding flesh act in concert to prevent the cable from disengaging from the groove during this passing operation. Once the cable is passed around the bone, the surgeon grasps both ends of the cable and withdraws the cable passer by reversing the insertion motion. In so doing, the cable is released from the passer without passing the instrument over either cable end. Therefore, the surgeon may insert the cable from either end of the cable passer groove without regard as to how the instrument will be removed.

Once the cable is passed beneath the bone, the surgeon inserts the free end of the cable through the hole in the ferrule from the flanged end and slides the ferrule down the length of cable to draw the cable tight against the bone. The surgeon should take care during this step to ensure that the free end is first inserted through the head portion of the ferrule, otherwise the ferrule will not properly seat against the bone.

Once the ferrule is seated, the surgeon threads the free end of the cable through the cable tensioner from the nipple end as depicted in FIG. 4. When the cable is exposed from the clamp end of the tensioner, the surgeon may pull the free end until the nipple seats against the ferrule and the cable is snugly drawn about the bone. Then the surgeon flips the cable clamp lever to the up position, thereby pivoting the cam and engaging it against the cable inside the inner member to clamp the tensioner to the cable. The surgeon grasps the grip of the tensioner in one hand and rotates the handle with the other until the desired cable tension is achieved. The combination crimper-cutters may then be taken in one hand and the crimper teeth placed around the short malleable tube section of the ferrule. As the grips of the crimper-cutter are brought together, the tube section deforms about the cable to thereby lock the cable in place. The tensioner may then be removed by lowering the cable clamp lever and withdrawing the tensioner over the free end of the cable. Lastly, the surgeon may trim the free end by inserting the cable into the cutter teeth of the combination crimper-cutters and bringing the grips together to cut the free end. A pair of cable straps thus installed is depicted in FIG. 1.

This procedure may be repeated as necessary so that a plurality of cables can be installed about the bone. Furthermore, the surgical instruments may be used in combination with other surgical instruments including those prior art instruments described above to achieve the same results. Thus, the cable system and surgical instruments may be used both in combination and separately.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A cable strap for banding a bone, said cable strap comprising:

a flexible cable for encircling the bone, said cable having at least two ends spaced by a length; and a fastener including a cable channel on an exterior surface pre-affixed to one of the cable ends, said cable end being threaded within said cable channel, said fastener being configured to be secured to said cable at a non-differentiated point along the cable length to thereby form a band about the bone, said fastener including a ferrule through which said cable is passed to form said band.

2. A method of manufacturing the cable strap of claim 1 for banding a bone, said method comprising the steps of:

providing the length of flexible cable having opposite ends;

providing the fastener being configured to secure said cable at another non-differentiated point along its length to form the band and attaching the fastener to one of said cable ends by threading said cable around said cable channel.

3. A method of manufacturing the cable strap of claim 1 for banding a bone, said method comprising the steps of:

providing the length of flexible cable having opposite ends and a diameter;

providing a ferrule having a malleable neck portion through which said flexible cable may be passed through and a head portion having a pair of annular flanges spaced by a distance substantially equal to the diameter of said flexible cable;

providing a malleable cable sleeve having an opening configured to accept two cable portions;

wrapping an end of the cable around the ferrule head portion and between the pair of annular flanges;

positioning the cable sleeve around the cable and adjacent the ferrule; and crimping the cable sleeve in place adjacent the ferrule to thereby attach the ferrule to the cable end.

4. A method for installing the cable strap of claim 1 around a bone, said method comprising the steps of:

providing said cable strap;

wrapping the cable strap around the bone;

drawing the cable tight around the bone; and fastening the fastener to the cable at said point to thereby secure the cable strap in place around the bone.

5. A surgical instrument kit having component parts capable of being used in combination to band a bone by passing the cable strap of claim 1 around the bone, tightening the cable around the bone, and fastening the cable in place about the bone, said kit comprising the combination of:

a plurality of said cable straps, each of said straps being comprised of the cable and the fastener pre-affixed thereto;

a cable passer for guiding the straps around the bone, said passer having an arcuate guiding member configured for insertion around the bone; and a cable tensioner configured to draw the cable tight around the bone.

6. The surgical instrument kit of claim 5 further comprising a cable cutter for trimming any excess cable after the cable strap is fastened in place.

7. The surgical instrument kit of claim 6 further comprising a crimper for fastening the fasteners around the cable to retain the cable strap in place around the bone.

8. The surgical instrument kit of claim 7 wherein the crimper and cutter are combined into a single instrument.

9. A method for tensioning the cable strap of claim 1 around a bone, said method comprising the steps of:

threading the cable through a tensioner;

clamping the cable to the tensioner; and screwing a tensioner handle with respect to a tensioner grip, said handle and grip being threaded together to thereby move the clamp away from the bone and tension the cable.

10. A cable strap for banding a bone, said cable strap comprising:

a flexible cable for encircling the bone, said cable having at least two ends spaced by a length;

a fastener pre-affixed to one of the cable ends, said fastener being configured to be secured to said cable at a point along the cable length to thereby form a band about the bone, said fastener including a ferrule through which said cable is passed to form said band; and a cable channel on said fastener, said one end cable end being positioned in said cable channel, said cable channel including a pair of spaced flanges, said one cable end being wrapped around said cable channel between said flanges and affixed so that said one cable end is securely pre-affixed to said fastener.

11. A cable strap for banding a bone, said cable strap comprising:

a flexible cable for encircling the bone, said cable having at least two ends spaced by a length;

a fastener pre-affixed to one of the cable ends, said fastener being configured to be secured to said cable at a point along the cable length to thereby form a band about the bone, said fastener including a ferrule through which said cable is passed to form said band, said ferrule including a hole through which said other cable end may be passed to thereby form the band of cable for encircling said bone; and a cable channel on said fastener, said one end cable end being positioned in said cable channel, said cable channel including a pair of spaced flanges, said one cable end being wrapped around said cable channel between said flanges and affixed so that said one cable end is securely pre-affixed to said fastener.

12. A cable strap for banding a bone, said cable strap comprising:

a flexible cable for encircling the bone, said cable having at least two ends spaced by a length;

a fastener pre-affixed to one of the cable ends, said fastener being configured to be secured to said cable at a point along the cable length to thereby form a band about the bone, said fastener including a ferrule through which said cable is passed to form said band, said ferrule including a hole through which said other cable end may be passed to thereby form the band of cable for encircling said bone, said ferrule being malleable so that it may be crimped to thereby secure it to said cable at said another point along its length; and a cable channel on said fastener, said one end cable end being positioned in said cable channel, said cable channel including a pair of spaced flanges, said one cable end being wrapped around said cable channel between said flanges and affixed so that said one cable end is securely pre-affixed to said fastener.

13. A cable strap for banding a bone, said cable strap comprising:

a flexible cable for encircling the bone, said cable having at least two ends spaced by a length;

a fastener pre-affixed to one of the cable ends, said fastener being configured to be secured to said cable at a point along the cable length to thereby form a band about the bone, said fastener including a ferrule through which said cable is passed to form said band, said ferrule including a hole through which said other cable end may be passed to thereby form the band of cable for encircling said bone, said ferrule being malleable so that it may be crimped to thereby secure it to said cable at said another point alone its length;

a cable channel on said fastener, said one end cable end being positioned in said cable channel, said cable channel including a pair of spaced flanges, said one cable end being wrapped around said cable channel between said flanges and affixed so that said one cable end is securely pre-affixed to said fastener; and a cable sleeve for securing said one cable end to said fastener.

14. A cable strap for banding a bone, said cable strap comprising:

a flexible cable for encircling the bone, said cable having at least two ends spaced by a length;

a fastener pre-affixed to one of the cable ends, said fastener being configured to be secured to said cable at a point along the cable length to thereby form a band about the bone, said fastener including a ferrule through which said cable is passed to form said band, said ferrule including a hole through which said other cable end may be passed to thereby form the band of cable for encircling said bone, said ferrule being malleable so that it may be crimped to thereby secure it to said cable at said another point along its length;

a cable channel on said fastener, said one end cable end being positioned in said cable channel, said cable channel including a pair of spaced flanges, said one cable end being wrapped around said cable channel between said flanges and affixed so that said one cable end is securely pre-affixed to said fastener; and a cable sleeve for securing said one cable end to said fastener, said cable sleeve configured to surround two cable diameters, said cable sleeve being malleable so that it may be crimped to thereby secure said cable diameters together.

15. A method for use with a cable strap for encircling a bone, the cable strap comprising a flexible cable having at least two ends spaced by a length for encircling the bone and a fastener pre-affixed to one of the cable ends, the fastener being configured to be secured to the cable at a point along the cable length to thereby form a band about the bone, the fastener including a ferrule through which said cable is passed to form said band, said method comprising the steps of:

providing a cable passer comprising a guide configured to guide the cable around the bone;

inserting said cable passer around the bone;

threading said cable through said guide and around said bone; and withdrawing the passer from around the bone and away from the cable without passing the passer of an and of the cable.

16. A method for use with a cable strap for encircling a bone, the cable strap comprising a flexible cable having at least two ends spaced by a length for encircling the bone and a fastener pre-affixed to one of the cable ends, the fastener being configured to be secured to the cable at a point along the cable length to thereby form a band about the bone, the fastener including a ferrule through which said cable is passed to form said band, said method for tensioning and affixing the cable strap around the bone and comprising the steps of:

inserting a cable passer around the bone, said cable passer having a cable guide therein;

passing said cable around said bone by threading said cable through said guide;

retaining the ends of said cable;

withdrawing the passer from around the bone without passing the passer over either end of the cable;

attaching a cable tensioner to the cable by actuating a clamp on the tensioner, said tensioner having a nipple for engaging said fastener ad a spreader for moving the clamp away from the nipple;

actuating the spreader to move the clamp away from the fastener and tighten the cable around the bone; and fastening said fastener to the cable to prevent the cable from loosening.

17. A cable strap for banding a bone, said cable strap comprising:

a flexible cable for encircling the bone, said cable having a pair of opposite ends; and a fastener including a cable channel on an exterior surface for receiving one of the cable ends, said fastener pre-affixed to one of the cable ends by joining the cable to said fastener, said cable threaded within said channel, said fastener including a ferrule though which the other of said cable ends is threaded to thereby form a loop, said ferrule being malleable so that as said ferrule is crimped said fastener is thereby fixedly secured to said cable at a non-differentiated point along the cable length to thereby band the bone.

18. The cable strap of claim 17 wherein said ferrule comprises a cylinder having a longitudinal axis, said cable end being secured to said fastener at an angle to said longitudinal axis.

19. The cable strap of claim 17 wherein said fastener includes a surface against which a tensioning tool may be placed for tensioning the cable.

20. The cable strap of claim 17 wherein said fastener lies substantially outside of said loop and not in contact with said bone as said cable strap is fastened about said bone.

* * * * *